US00PP17693P2

(12) United States Plant Patent
Fischer-Töhl

(10) Patent No.: US PP17,693 P2
(45) Date of Patent: May 1, 2007

(54) ***GERANIUM* PLANT NAMED 'BALFANWITE'**

(50) Latin Name: *Pelargonium×hortorum*
Varietal Denomination: Balfanwite

(75) Inventor: Ilse Fischer-Töhl, Kirchlinteln (DE)

(73) Assignee: Silze GmbH & Company KG, Weener (DE)

( * ) Notice: Subject to any disclaimer, the term of this patent is extended or adjusted under 35 U.S.C. 154(b) by 0 days.

(21) Appl. No.: 11/272,545

(22) Filed: Nov. 10, 2005

(51) Int. Cl.
*A01H 5/00* (2006.01)

(52) U.S. Cl. ..... Plt./326
(58) Field of Classification Search ..... Plt./326
See application file for complete search history.

*Primary Examiner*—Kent Bell
*Assistant Examiner*—June Hwu
(74) *Attorney, Agent, or Firm*—Audrey Charles

(57) ABSTRACT

A new and distinct cultivar of *Geranium* plant named 'Balfanwite' characterized by its semi-double white-colored flowers, dark green-colored foliage, and medium to compact, upright growth habit.

2 Drawing Sheets

Latin name of genus and species of plant claimed: *Pelargonium×hortorum.*
Variety denomination: 'Balfanwite'.

BACKGROUND OF THE INVENTION

The present invention relates to a new and distinct cultivar of *Geranium* plant botanically known as *Pelargonium× hortorum* and hereinafter referred to by the cultivar name 'Balfanwite'.

The new cultivar originated in a controlled breeding program in Weener, Niedersachen (Northern Germany) during the summer of 1999. The objective of the breeding program was the development of *Geranium* cultivars that flower uniformly and have large flowers, dark green-colored foliage, and a vigorous, upright growth habit.

The female (seed) parent of the new cultivar was 'Penwei' (HU9801865 A2 and QZ1995/0756). The male (pollen) parent of the new cultivar was 'Sel Wenke', not patented. The new *Geranium* was discovered and selected by the inventor as a single flowering plant within the progeny of the above stated cross-pollination during June 2000 in a controlled environment at Weener, Niedersachen.

Asexual reproduction of the new cultivar by terminal stem cuttings since June 2000 at Weener, Niedersachen and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfanwite' as a new and distinct cultivar of *Geranium* plant:

1. Semi-double white-colored flowers;
2. Dark green-colored foliage; and
3. Medium to compact, upright growth habit.

Plants of the new cultivar differ from plants of the female parent primarily in flower shape and growth habit and from plants of the male parent primarily in leaf color and growth habit.

Of the many commercially available *Geranium* cultivars known to the inventor, the most similar in comparison to the new cultivar is 'Fisrowi', U.S. Plant Pat. No. 12,389. However, in side by side comparisons, plants of the new cultivar differ from plants of 'Fisrowi' in the following characteristics:

1. Plants of the new cultivar are more compact as measured by plant height than plants of 'Fisrowi'; and
2. Plants of the new cultivar have darker foliage color than plants of 'Fisrowi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfanwite'. The plants were grown in 10 cm pots for 10 weeks in a greenhouse at West Chicago, Ill.

DETAILED BOTANICAL DESCRIPTION

Figure 1:
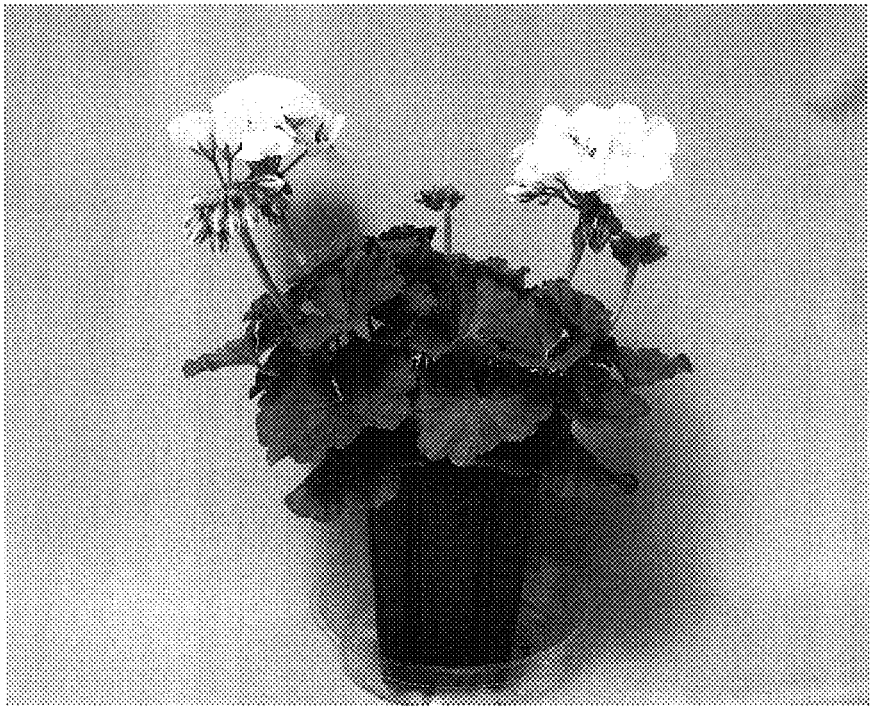
FIG. 1 illustrates a side view of the overall growth and flowering habit of 'Balfanwite'.
Figure 2:
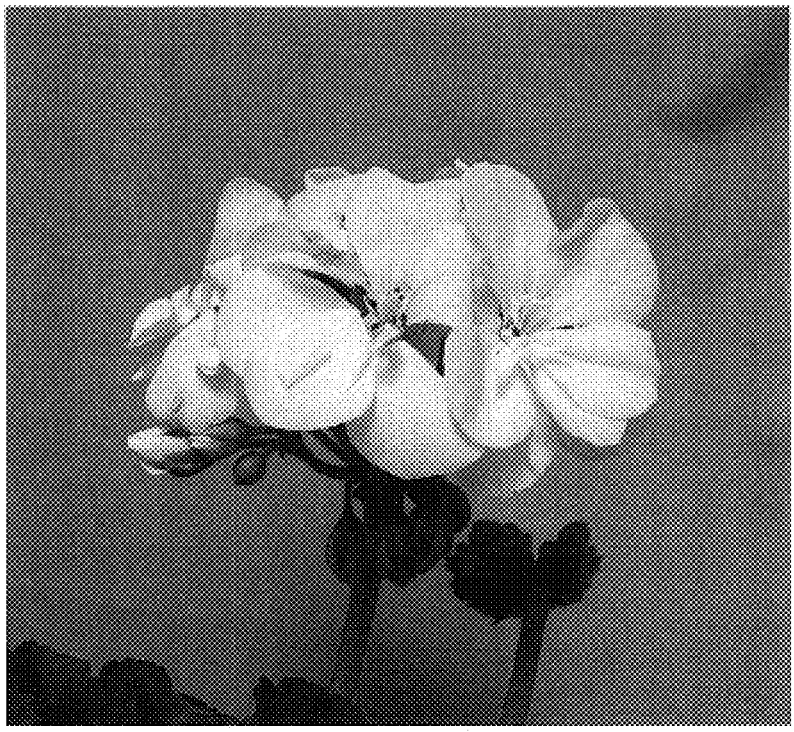
FIG. 2 illustrates a close-up view of a single umbel of 'Balfanwite'.
Figure 3:
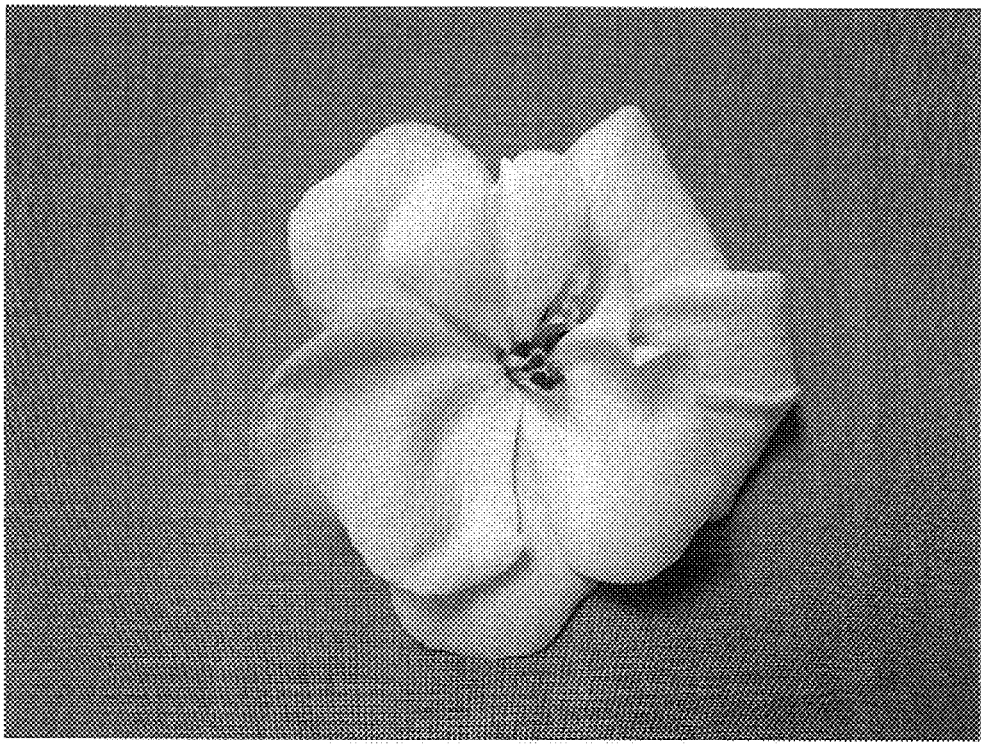
FIG. 3 illustrates a close-up view of a single floret of 'Balfanwite'.
Figure 4:
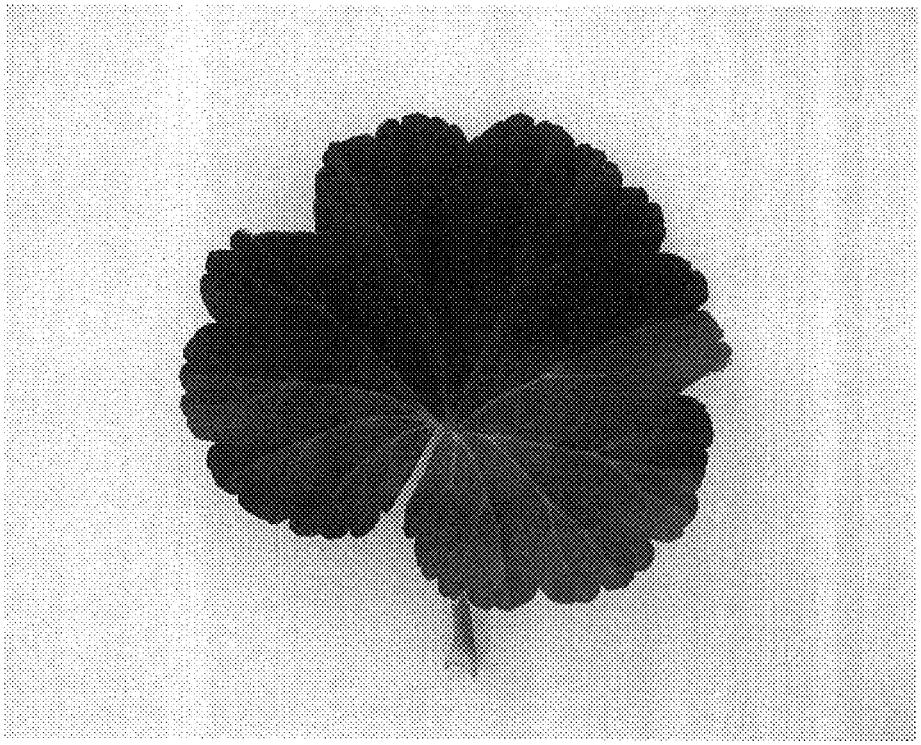
FIG. 4 illustrates a close-up view of a single leaf of 'Balfanwite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 23, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 10 weeks utilizing a soilless growth medium. Greenhouse temperatures were maintained at approximately 65° F. to 75° F. (18° C. to 24° C.) during the day and approximately 62° F. to 68° F. (17° C. to 20° C.) during the night. Greenhouse light levels of 3,500 to 6,000 footcandles were maintained during the day.

Botanical classification: *Pelargonium×hortorum* cultivar Balfanwite.

Parentage:

*Female parent.*—'Penwei', not patented.

*Male parent.*—'Sel Wenke', not patented.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 to 9 weeks from a rooted cutting.

*Growth habit and general appearance.*—Medium to compact, upright.

*Size.*—Height from soil level to top of plant plane: Approximately 20.4 cm. Height from soil level to top of foliage: Approximately 11.3 cm. Width: Approximately 25.0 cm.

*Branching habit.*—Freely basal branching. Approximately 3 branches per plant.

*Branch.*—Strength: Strong. Length: Approximately 7.0 cm. Diameter: Approximately 7.2 mm. Texture: Densely glandular-pubescent. Stem color: 144A. Gland color: Colorless and transparent. Internode length at center of branch: Approximately 1.5 cm.

*Foliage.*—Number of leaves per lateral branch: Approximately 14. Fragrance: None. Form: Simple. Arrangement: Opposite. Aspect: At acute angle to stem. Shape: Reniform. Margin: Bicrenate. Apex: Rounded. Base: Cordate. Venation pattern: Palmate. Length of mature leaf: Approximately 4.7 cm. Width of mature leaf: Approximately 8.2 cm. Texture of upper and lower surfaces: Mixture of strigose and stipulate glandular pubescence. Color of upper surface of mature foliage: Closest to 147A at margin and at petiole attachment point with a zone of darker than 147A at center of leaf; venation of 143B. Color of lower surface of mature foliage: Closest to 147B with venation of 145A. Petiole length: Approximately 4.4 cm. Petiole diameter: Approximately 2.2 mm. Petiole texture: Mixture of strigose and stipulate glandular pubescence. Petiole color: Closest to 144A. Gland color: Colorless, transparent.

Flowering description:

*Flowering habit.*—'Balfanwite' is freely flowering under outdoor growing conditions with substantially continuous blooming from spring through autumn and year round in greenhouse environment.

*Time to first flower.*—Approximately 10.6 weeks from sticking of unrooted cutting.

*Lastingness of individual floret.*—Approximately 5 to 7 days.

Inflorescence description:

*Type.*—Umbel. Position: Above foliage. Number of open umbels at 10 weeks: Approximately 2. Number of developing umbels at 10 weeks: Approximately 2. Umbel diameter: Approximately 9.5 cm. Umbel height/depth: Approximately 5.7 cm. Number of fully open florets per umbel: Approximately 8. Fragrance: None.

*Peduncle.*—Strength: Strong. Aspect: Erect. Length: Approximately 13.3 cm. Diameter: Approximately 3.6 mm. Texture: Mixture of strigose and stipulate glandular pubescence. Peduncle color: Closest to 144A. Gland color: Colorless and transparent.

Flower description:

*Bud rate of opening.*—Generally takes 3 to 5 days for bud to progress from first color to fully open flower.

*Bud just before opening.*—Shape: Elliptic. Length: Approximately 1.3 cm. Diameter: Approximately 7.5 mm. Sepal color: 144B. Petal color: 155C. Sepal texture: Densely glandular-pubescent. Petal texture: Glabrous. Gland color: Colorless and transparent.

*Corolla.*—Form: Semi-double. Shape: Round. Diameter: Approximately 5.0 cm. Depth: Approximately 2.2 cm.

*Petals/petaloids.*—Quantity: Approximately 7 petals and 2 to 3 irregular shaped petaloids per flower. Appearance: Iridescent. Aspect: Slightly cupped. Arrangement: Imbricate. Shape: Obovate. Apex: Obtuse. Base: Attenuate. Margin: Entire. Texture of upper and lower surfaces: Glabrous. Length of upper petal: Approximately 2.9 cm. Width of upper petal: Approximately 2.2 cm. Length of lower petal: 2.7 cm. Width of lower petal: 2.3 cm. Color of upper and lower surfaces of upper and lower petals: Closest to 155C.

*Pedicel.*—Strength: Strong. Angle: Acute to stem. Length: Approximately 3.3 cm. Diameter: Approximately 4.9 mm. Texture: Densely glandular-pubescent. Color: 144A. Gland Color: 21C.

*Calyx.*—Shape: Five-pointed star. Width: Approximately 2.1 cm.

*Sepals.*—Quantity per floret: 5. Shape: Lanceolate. Apex: Acuminate: Margin: Entire. Upper sepal length: Approximately 1.3 cm. Upper sepal width: Approximately 3.7 mm. Lower sepals length: Approximately 1.2 cm. Lower sepals width: Approximately 2.6 mm. Texture of upper surface: Glabrous. Texture of lower surface: Glandular-pubescence. Color of upper and lower surface: 144B. Gland color: Colorless, transparent with a pale orange-colored tint.

*Reproductive organs.*—Androecium: Quantity of mature anthers: Approximately 8 per flower: Anther shape: Oval. Anther length: Approximately 2.0 mm. Anther color: 29D. Pollen amount: Abundant. Pollen color N25A. Gynoecium: Pistil quantity: One per floret. Pistil length: Approximately 9.3 mm. Stigma shape: Five branched. Stigma length: Approximately 1.8 mm. Stigma color: 150D. Style length: Approximately 2.5 mm. Style color: 145C. Ovary length: Approximately 5.0 mm. Ovary texture: Sericeous. Ovary color: 143B.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Balfanwite', substantially as herein shown and described.

* * * * *